United States Patent
Riina et al.

(10) Patent No.: US 9,295,818 B2
(45) Date of Patent: Mar. 29, 2016

(54) METHOD AND APPARATUS FOR ACCESSING THE WALL OF A VASCULAR STRUCTURE OR OTHER BODY LUMEN WHILE SIMULTANEOUSLY PROVIDING ZONE ISOLATION AND FLUID BYPASS CAPABILITY

(75) Inventors: Howard Riina, Scarsdale, NY (US); Jeffrey Milsom, New York, NY (US); J. Fredrick Cornhill, New York, NY (US); Robert Andrews, Norfolk, MA (US); Clair L. Strohl, Norfolk, MA (US); Edward L. Dickinson, Littleton, MA (US)

(73) Assignee: Cornell University, Ithaca, NY (US)

( * ) Notice: Subject to any disclaimer, the term of this patent is extended or adjusted under 35 U.S.C. 154(b) by 1599 days.

(21) Appl. No.: 12/481,776

(22) Filed: Jun. 10, 2009

(65) Prior Publication Data

US 2010/0076365 A1    Mar. 25, 2010

Related U.S. Application Data

(60) Provisional application No. 61/189,670, filed on Aug. 21, 2008.

(51) Int. Cl.
*A61M 25/10*    (2013.01)
*A61B 17/12*    (2006.01)
*A61M 29/02*    (2006.01)

(52) U.S. Cl.
CPC ...... *A61M 25/1011* (2013.01); *A61B 17/12022* (2013.01); *A61B 17/12036* (2013.01);
(Continued)

(58) Field of Classification Search
CPC .................. A61M 25/1011; A61B 17/12022; A61B 17/12136

USPC ............ 606/191, 192, 194, 198; 604/103.07, 604/101.01, 101.03, 101.05
See application file for complete search history.

(56) References Cited

U.S. PATENT DOCUMENTS

| | | | |
|---|---|---|---|
| 4,183,102 A |   | 1/1980 | Guiset |
| 4,456,011 A | * | 6/1984 | Warnecke ............... 604/101.05 |

(Continued)

FOREIGN PATENT DOCUMENTS

| | | |
|---|---|---|
| WO | WO95/05209 | 2/1995 |
| WO | WO98/08558 | 3/1998 |
| WO | WO00/74749 | 12/2000 |

*Primary Examiner* — Brian Pellegrino
(74) *Attorney, Agent, or Firm* — Pandiscio & Pandiscio

(57) ABSTRACT

Apparatus and method for accessing the wall of a body lumen while simultaneously providing zone isolation and fluid bypass capability, the apparatus comprising:
an erectable proximal isolation barrier capable of making a sealing engagement with the wall of the body lumen;
an erectable distal isolation barrier capable of making a sealing engagement with the wall of the body lumen;
a bypass channel secured to, and extending between, the proximal isolation barrier and the distal isolation barrier, the bypass channel comprising a lumen communicating with the region proximal to the proximal isolation barrier and with the region distal to the distal isolation barrier; and
a working catheter passing through the proximal isolation barrier and terminating short of the distal isolation barrier, the working catheter providing a central lumen for providing access to the wall of the body lumen between the proximal isolation barrier and the distal isolation barrier.

55 Claims, 13 Drawing Sheets

(52) U.S. Cl.
CPC ..... *A61B17/12045* (2013.01); *A61B 17/12113* (2013.01); *A61B 17/12136* (2013.01); *A61M 29/02* (2013.01); *A61B 2017/1205* (2013.01); *A61B 2017/12127* (2013.01); *A61M 2025/1052* (2013.01); *A61M 2025/1095* (2013.01); *A61M 2205/0266* (2013.01)

(56) References Cited

U.S. PATENT DOCUMENTS

| | | | |
|---|---|---|---|
| 4,832,688 A * | 5/1989 | Sagae et al. | 606/194 |
| 5,135,484 A | 8/1992 | Wright | |
| 5,287,857 A | 2/1994 | Mann | |
| 5,514,092 A * | 5/1996 | Forman et al. | 604/101.03 |
| 5,554,119 A * | 9/1996 | Harrison et al. | 604/103.01 |
| 5,556,389 A * | 9/1996 | Liprie | 606/192 |
| 5,674,198 A | 10/1997 | Leone | |
| 5,716,340 A | 2/1998 | Schweich, Jr. et al. | |
| 6,139,517 A | 10/2000 | Macoviak et al. | |
| 6,214,022 B1 | 4/2001 | Taylor et al. | |
| 6,287,321 B1 * | 9/2001 | Jang | 604/101.01 |
| 6,913,610 B2 * | 7/2005 | Nakao | 606/192 |
| 6,936,057 B1 | 8/2005 | Nobles | |
| 7,105,031 B2 | 9/2006 | Letort | |
| 8,147,449 B2 * | 4/2012 | Gobel et al. | 604/103.07 |
| 2003/0088246 A1 | 5/2003 | Swartz et al. | |
| 2004/0068226 A1 | 4/2004 | Brannon | |
| 2004/0225251 A1 | 11/2004 | Glickman | |
| 2005/0085770 A1 | 4/2005 | Don Michael | |
| 2005/0245893 A1 | 11/2005 | Leschinsky | |
| 2005/0267407 A1 | 12/2005 | Goldman | |
| 2006/0200191 A1 | 9/2006 | Zadno-Azizi | |
| 2007/0213761 A1* | 9/2007 | Murphy et al. | 606/194 |
| 2010/0016833 A1* | 1/2010 | Ogle | A61B 17/12022 604/509 |

* cited by examiner

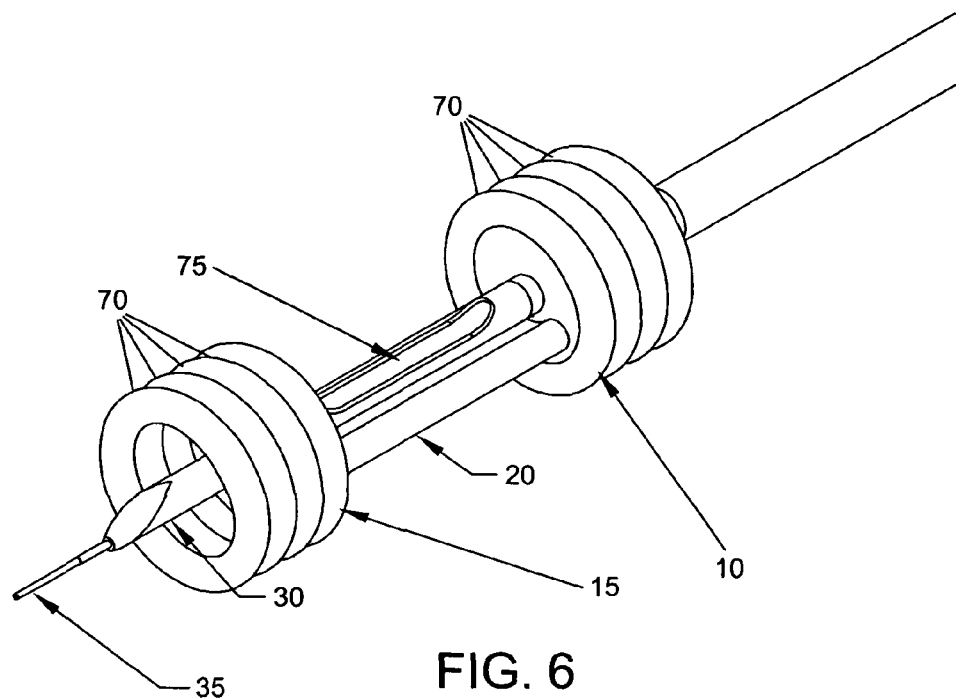
FIG. 6
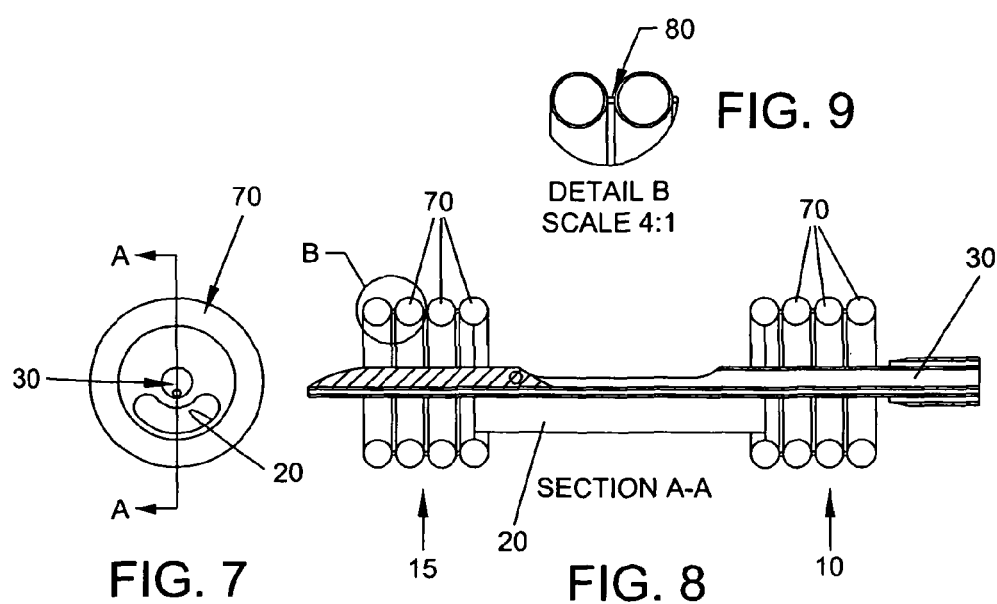
FIG. 9
FIG. 7
FIG. 8

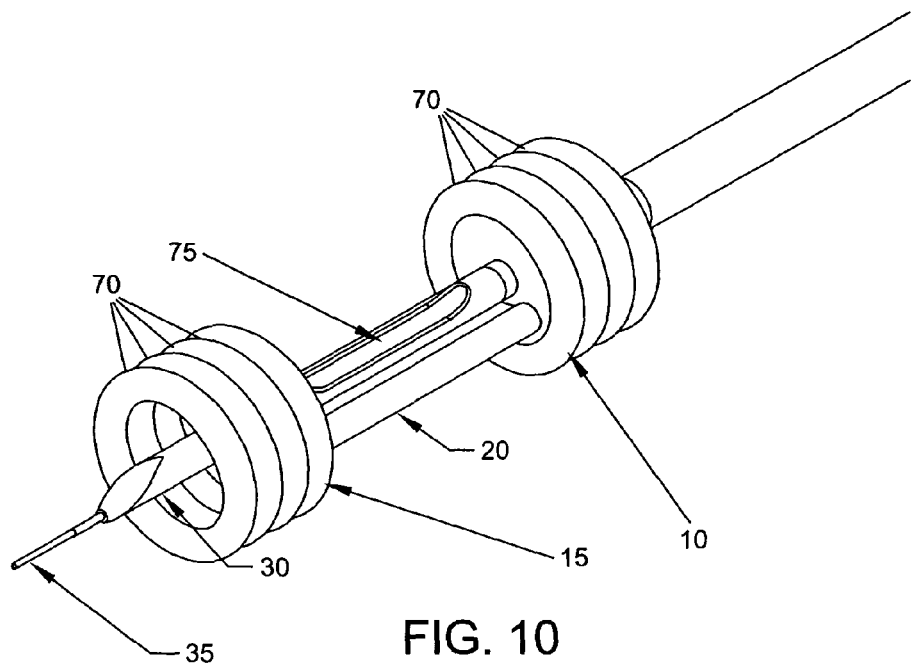
FIG. 10
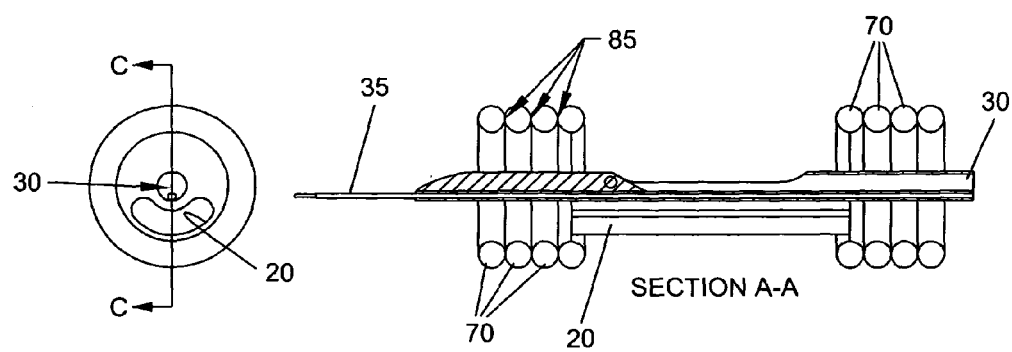
FIG. 11
FIG. 12

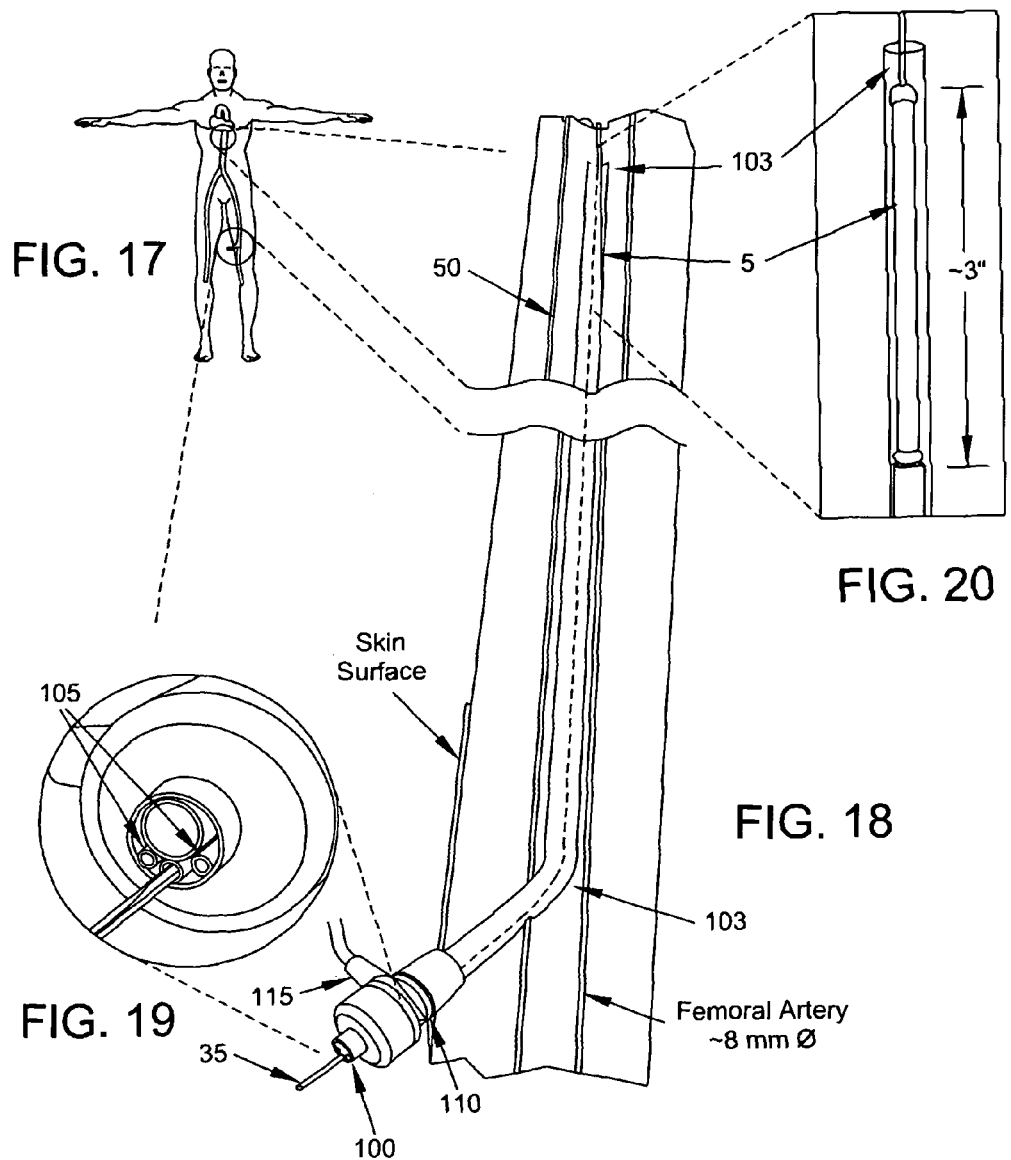

METHOD AND APPARATUS FOR ACCESSING THE WALL OF A VASCULAR STRUCTURE OR OTHER BODY LUMEN WHILE SIMULTANEOUSLY PROVIDING ZONE ISOLATION AND FLUID BYPASS CAPABILITY

REFERENCE TO PENDING PRIOR PATENT APPLICATION

This patent application claims benefit of prior U.S. Provisional Patent Application Ser. No. 61/189,670, filed Aug. 21, 2008 by Howard Riina et al. for METHOD AND APPARATUS FOR ACCESSING THE SIDE WALL OF A VASCULAR STRUCTURE OR OTHER BODY LUMEN, ORGAN OR TUBULAR STRUCTURE WHILE SIMULTANEOUSLY PROVIDING ZONE ISOLATION AND BYPASS CAPABILITY, which patent application is hereby incorporated herein by reference.

FIELD OF THE INVENTION

This invention relates to medical procedures and apparatus in general, and more particularly to medical procedures and apparatus for accessing the wall of a vascular structure or other body lumen.

BACKGROUND OF THE INVENTION

Medical technologies are now expanding so that curative therapies may now be applied directly to the wall of a vascular structure or other body lumen (e.g., tubular structure or organ) within the human body. In most situations it will be necessary to access the inside (or other portion) of the wall of a vascular structure or other body lumen in order to provide therapy to a patient. By way of example but not limitation, it may be necessary to treat an aneurysm formed in the wall of an artery (e.g., a lateral aneurysm such as a saccular aneurysm, a fusiform aneurysm such as a typical abdominal aortic aneurysm), or to treat a lesion formed on the wall of a vascular structure (e.g., an artery or vein) or other tubular or hollow structure. As used herein, the term "vascular structure" is intended to encompass any tubular or hollow structure of the vasculature (e.g., an artery, a vein, a blood chamber, etc.), and the term "body lumen" is intended to encompass any tubular or hollow structure, including the gastrointestinal or genitourinary tracts, the lymph system, an air passageway, the interior of a hollow organ, a passageway through a body structure, etc. As used herein, the term "wall" of a vascular structure or other body lumen is intended to encompass the inside surface of the wall and/or any other portion of the wall, including aneurysms, lesions, etc. which may be formed in or on the wall.

Additionally, in many situations it may be desirable to isolate a segment of the vascular structure (or other body lumen) from the remainder of the vascular structure (or other body lumen). By way of example but not limitation, a particular therapy applied to the inside of the wall of a vascular structure may create debris which should be localized and prevented from flowing downstream from the site of the therapy.

Furthermore, in many situations it may become necessary to apply therapy to the inside of the wall of a vascular structure (or other body lumen) without interrupting the flow of blood (or other fluids) through the vascular structure (or other body lumen).

Thus, there is a substantial need for a novel method and apparatus for accessing the wall of a vascular structure or other body lumen while simultaneously providing "zone isolation" and simultaneously providing fluid bypass capability. Ideally, pressure and fluid (presence or absence) should be controllable within the isolation zone, thereby facilitating the use of medical instruments (including cutting instruments, biopsy instruments, closure instruments, endoscopic visualization, etc.), vacuum, electrical energy (e.g., electrosurgery), adhesives and/or other therapies which may be difficult to apply in a zone where blood or any other biologic fluid or substance is present and/or flowing.

SUMMARY OF THE INVENTION

The present invention provides a novel method and apparatus for accessing the wall of a vascular structure or other body lumen while simultaneously providing zone isolation and simultaneously providing fluid bypass capability.

In one preferred form of the invention, the novel method and apparatus permits pressure and fluid (presence or absence) to be controllable within the isolation zone, thereby facilitating the use of medical instruments (including cutting instruments, biopsy instruments, closure instruments, material delivery systems, endoscopes, etc.), vacuum, electrical energy (e.g., electrosurgery), adhesives and/or other therapies (e.g., agents promoting thrombus, gene therapeutic agents, etc.) which may be difficult to apply in a zone where blood or another biologic fluid or substance is present and/or flowing.

More particularly, the present invention comprises the provision and use of an access system comprising an erectable proximal isolation barrier (e.g., a balloon, a superelastic shape memory alloy ring, etc.), an erectable distal isolation barrier (e.g., a balloon, a superelastic shape memory alloy ring, etc.), and a bypass channel extending between the proximal isolation barrier and the distal isolation barrier, such that when the access system is erected in a body lumen, the access system can isolate a segment of the body lumen from the remainder of the body lumen, while still permitting a fluid to flow independently through the isolated segment of the body lumen. Additionally, the access system preferably comprises a working catheter extending through the proximal isolation barrier and providing access (e.g., for instruments, etc.) to the wall of the isolated segment of the body lumen. Furthermore, the access system can be configured so as to be mountable on a guidewire, so that the access system can be delivered over a guidewire to a desired position within a body lumen.

In one preferred form of the present invention, there is provided apparatus for accessing the wall of a body lumen while simultaneously providing zone isolation and fluid bypass capability, the apparatus comprising:

an erectable proximal isolation barrier capable of making a sealing engagement with the wall of the body lumen;

an erectable distal isolation barrier capable of making a sealing engagement with the wall of the body lumen;

a bypass channel secured to, and extending between, the proximal isolation barrier and the distal isolation barrier, the bypass channel comprising a lumen communicating with the region proximal to the proximal isolation barrier and with the region distal to the distal isolation barrier; and a working catheter passing through the proximal isolation barrier and terminating short of the distal isolation barrier, the working catheter providing a central lumen for providing access to the wall of the body lumen between the proximal isolation barrier and the distal isolation barrier.

In another preferred form of the present invention, there is provided a method for accessing the wall of a body lumen while simultaneously providing zone isolation and fluid bypass capability, the method comprising:

providing an access system comprising:
an erectable proximal isolation barrier capable of making a sealing engagement with the wall of the body lumen;
an erectable distal isolation barrier capable of making a sealing engagement with the wall of the body lumen;
a bypass channel secured to, and extending between, the proximal isolation barrier and the distal isolation barrier, the bypass channel comprising a lumen communicating with the region proximal to the proximal isolation barrier and with the region distal to the distal isolation barrier; and
a working catheter passing through the proximal isolation barrier and terminating short of the distal isolation barrier, the working catheter providing a central lumen for providing access to the wall of the body lumen between the proximal isolation barrier and the distal isolation barrier;
deploying the access system within the body lumen;
erecting the distal isolation barrier and the proximal isolation barrier; and
accessing the wall of the body lumen through the working catheter.

As noted above, the present invention provides a novel method and apparatus for accessing the wall of a vascular structure or other body lumen while simultaneously providing zone isolation and fluid bypass capability. In the following description, the present invention may sometimes hereinafter be discussed in the context of application to a vascular structure, however, it should be appreciated that this is done solely for the sake of clarity of illustration and should not be considered as limiting the scope of the present invention. Thus, the present invention may also be used in conjunction with body lumens other than vascular structures, e.g., the gastrointestinal or genitourinary tracts, the lymph system, an air passageway, the interior of a hollow organ, a passageway through a body structure, etc.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 6 is a schematic perspective view showing an alternative form of an access system;

FIG. 7 is a schematic end view of the access system shown in FIG. 6;

FIG. 8 is a schematic sectional view taken along line A-A of FIG. 7;

FIG. 9 is a schematic enlarged view of the segment labeled B in FIG. 8;

FIG. 10 is a schematic perspective view showing an alternative form of an access system;

FIG. 11 is a schematic end view of the access system shown in FIG. 10;

FIG. 12 is a schematic sectional view taken along line C-C of FIG. 11; and

FIGS. 13, 14, 14A and 15-20 illustrate a delivery catheter which may used to deploy the access system of the present invention at a procedure site within a vascular structure.

DETAILED DESCRIPTION OF THE PREFERRED EMBODIMENTS

Figure 1:
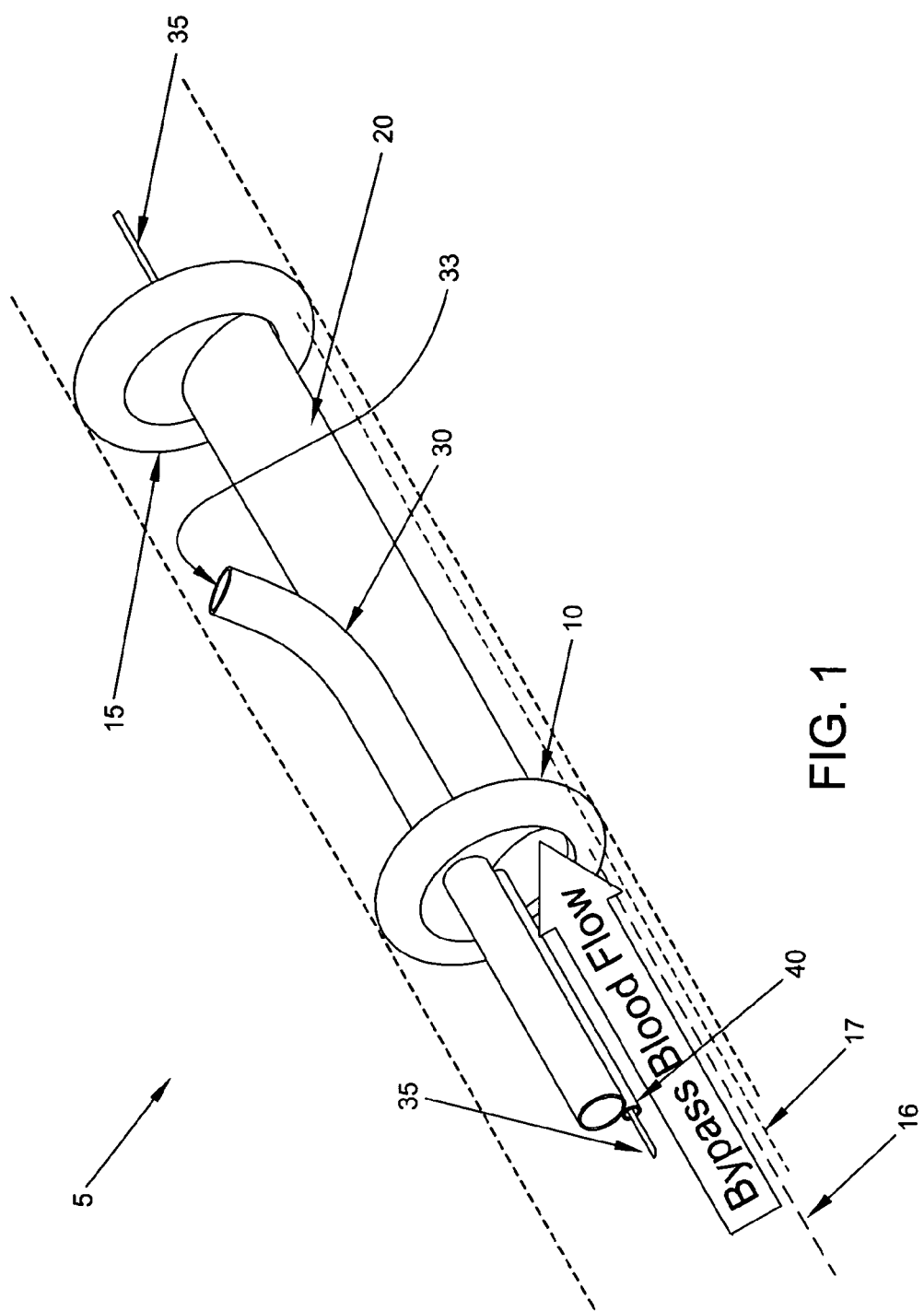
FIG. 1 is a schematic perspective view showing the access system of the present invention deployed within a vascular structure.
Figure 2:
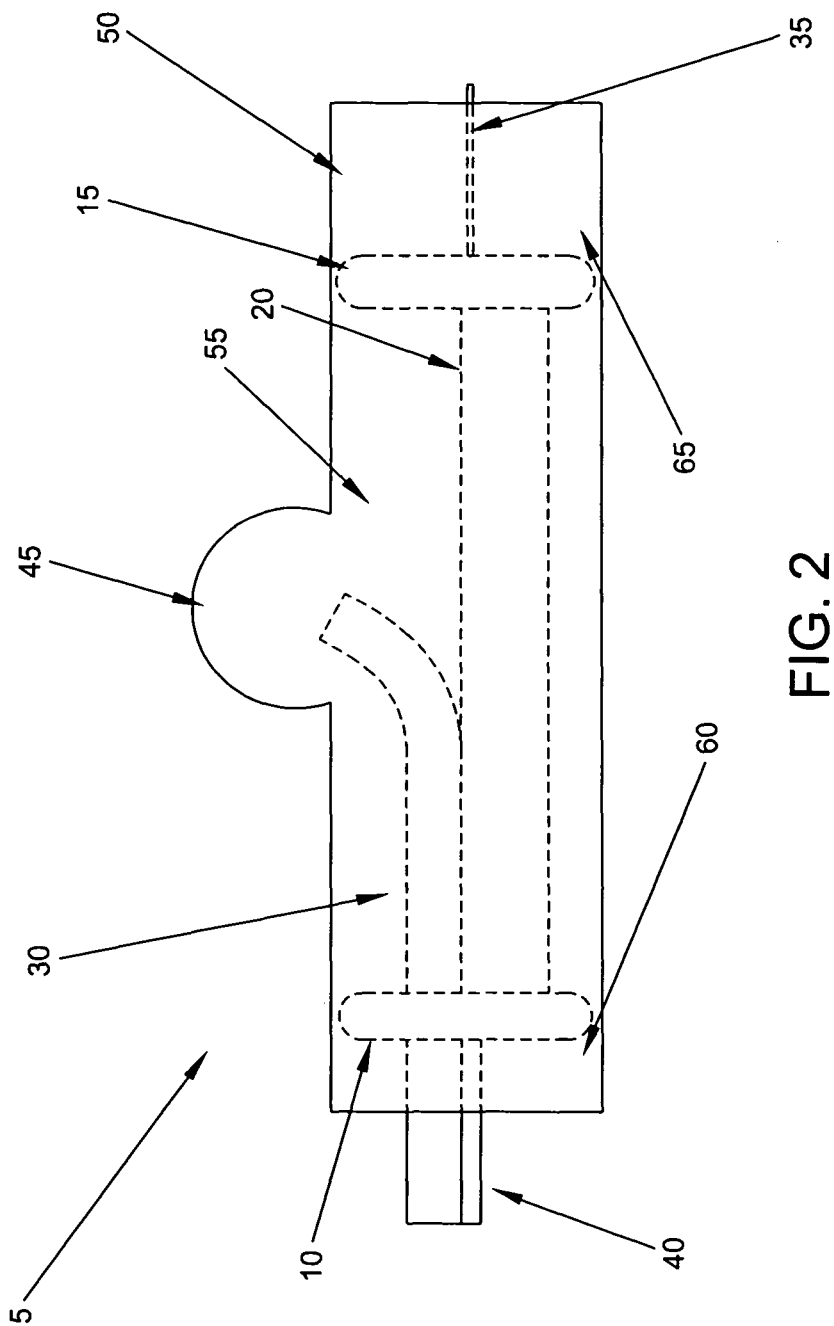
FIG. 2 is a schematic side view showing the access system of FIG. 1 deployed within a vascular structure, wherein the vascular structure includes an aneurysm.
Figure 3:
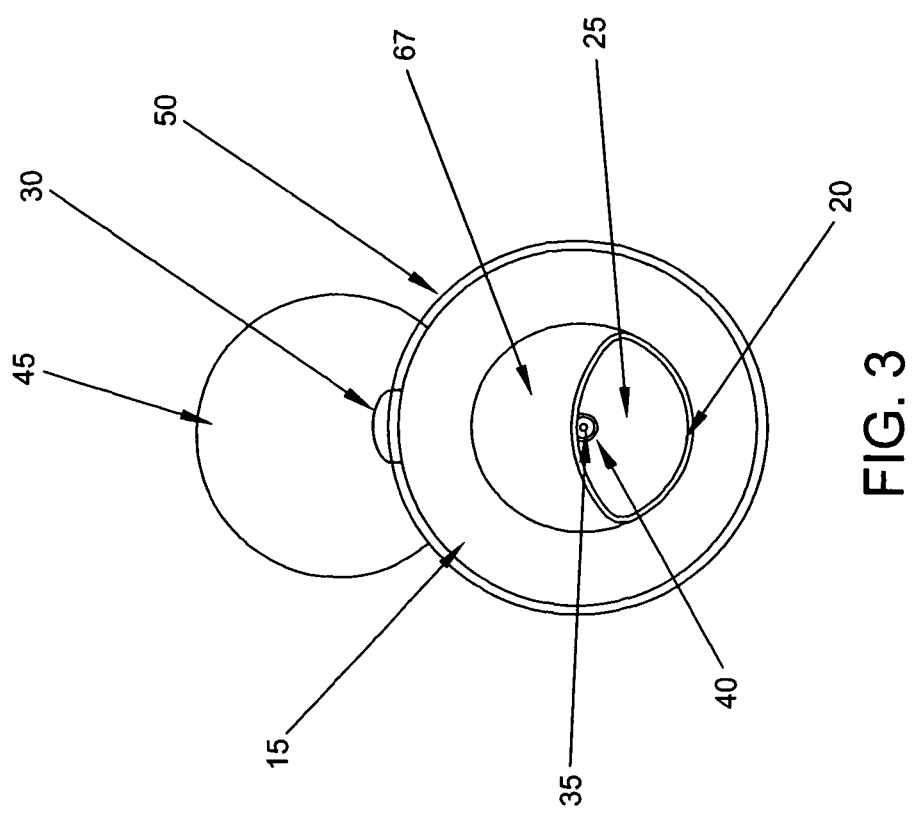
FIG. 3 is a schematic end view, as seen from the distal end, showing the access system of FIG. 1 deployed within the vascular structure shown in FIG. 2.

Looking first at FIGS. 1-3, there is shown an access system 5 formed in accordance with the present invention. Access system 5 generally comprises an erectable proximal isolation barrier 10 and an erectable distal isolation barrier 15 for disposition within the lumen of a vascular structure or other body lumen. Erectable proximal isolation barrier 10 and erectable distal isolation barrier 15 are formed so that they can (i) initially assume a diametrically-reduced configuration so as to facilitate insertion of access system 5 to a site where a procedure (e.g., therapy, diagnosis, exploration, etc.) is to be conducted, and (ii) thereafter assume a diametrically-expanded configuration once at the procedure site so as to form a fluid-tight (occlusive) seal against the wall of the vascular structure, whereby to isolate a segment of the vascular structure from the remainder of the vascular structure, e.g., while a procedure is performed. In one preferred form of the invention, proximal isolation barrier 10 and distal isolation barrier 15 have a peripheral surface texture to help ensure that the barriers will maintain their position in the vascular structure once deployed. By way of example but not limitation, such peripheral surface texturing may comprise dimpling, circumferential ribbing, etc. In this respect it will be appreciated that the proximal and distal isolation barriers should remain in place when systolic pressure is present on the outer surfaces of each of the isolation barriers and atmospheric pressure is present within the isolated segment of the vascular structure. Furthermore, erectable proximal isolation barrier 10 and erectable distal isolation barrier 15 are formed so that they may be collapsed when desired so as to facilitate removal of access system 5 from the vascular structure, e.g., at the conclusion of the procedure. By way of example but not limitation, erectable proximal isolation barrier 10 and erectable distal isolation barrier 15 may be formed by inflatable/deflatable balloons, compressible/expandable superelastic shape memory alloy (e.g., Nitinol) rings, etc. As a result of this construction, when access system 5 has been deployed at a desired point in a vascular structure or other body lumen, and erectable proximal isolation barrier 10 and erectable distal isolation barrier 15 have been expanded to their sealing condition, access system 5 can isolate a segment of the vascular structure (i.e., the portion located between erected proximal isolation barrier 10 and erected distal isolation barrier 15) from the remainder of the vascular structure, e.g., while a procedure is performed. This can be important in a variety of situations, e.g., where the procedure may dislodge debris which could harm downstream tissue.

Access system 5 is preferably constructed so that erectable proximal isolation barrier 10 and erectable distal isolation barrier 15 may be diametrically-expanded and diametrically-reduced independently of one another. In other words, access system 5 is preferably constructed so that proximal isolation barrier 10 may be diametrically-expanded or diametrically-reduced regardless of the condition of distal isolation barrier 15, and vice-versa.

Where erectable proximal isolation barrier 10 and erectable distal isolation barrier 15 are formed out of an inflatable/deflatable balloon, access system 5 also comprises channels for delivering fluid (a liquid or a gas) for inflating/deflating the balloons. By way of example but not limitation, a channel 16 may be provided for inflating the balloon of erectable proximal isolation barrier 10 and a channel 17 may be provided for inflating the balloon of erectable distal isolation barrier 15.

Access system 5 further comprises a bypass channel 20 secured to, and extending between and through, proximal isolation barrier 10 and distal isolation barrier 15. Bypass channel 20 comprises a central lumen 25 (FIG. 3) which opens proximal to proximal isolation barrier 10 and distal to distal isolation barrier 15, whereby to permit flow from one side of access system 5 to the other side of access system 5. As a result of this construction, when access system 5 is deployed in a vascular structure so as to isolate a segment of the vascular structure from the remainder of the vascular structure, access system 5 can still permit blood to flow uninterrupted through the bypass channel 20 which traverses the isolated segment of the vascular structure. This can be important in a variety of physiologic situations, e.g., such as where continued blood flow is important for the oxygenation of downstream tissues.

In one embodiment, the upstream isolation barrier may be configured so as to channel blood flow into bypass channel 20. Thus, for example, in FIG. 1, proximal isolation barrier 10 may be configured so as to channel blood flow into bypass channel 20. By way of example but not limitation, the upstream side of proximal isolation barrier 10 may be formed with a concave (e.g., funnel-shaped) surface surrounding the entrance to bypass channel 20.

Thus it will be seen that access system 5 provides both zone isolation (via proximal isolation barrier 10 and distal isolation barrier 15) and distal perfusion (via bypass channel 20). These features can be important in a variety of situations where zone isolation and distal perfusion are both desirable and/or necessary, e.g., where vascular trauma needs to be temporarily stabilized while the patient is transported to another site for further treatment, where an aneurysm (e.g., abdominal or thoracic, iliac or femoral, etc.) is bleeding and/or threatening to rupture, or actually has ruptured, etc. Furthermore, it should be appreciated that access system 5 may be used on both the arterial and venous sides of the circulation system.

Access system 5 further comprises a working catheter 30 which passes through proximal isolation barrier 10 and provides access (e.g., for medical instruments including but not limited to cutting instruments, biopsy instruments, closure instruments, material delivery systems, endoscopes, etc., including for the delivery of adhesives and/or agents for promoting thrombus, gene therapeutic agents, etc.) to the wall of the isolated length of the vascular structure. Preferably, working catheter 30 can slide forward and backward through proximal isolation barrier 10 such that working catheter 30 can be positioned anywhere between proximal isolation barrier 10 and distal isolation barrier 15. Additionally, access system 5 is preferably configured so that working catheter 30 can be rotated in order that the distal tip 33 of working catheter 30 can access substantially the entire circumference of the isolated vessel.

Access system 5 is preferably configured so as to be mountable on a guidewire 35, so that access system 5 may be delivered to a desired position within the vascular structure. By way of example but not limitation, access system 5 may comprise a guidewire channel 40 mounted to proximal isolation barrier 10 and/or working catheter 30 (e.g., proximal to proximal isolation barrier 10, as shown in FIG. 1), such that guidewire 35 may be received within bypass channel 20 and guidewire channel 40, whereby to permit controlled delivery of access system 5 to a desired location within a vascular structure.

In one preferred form of use, and looking now at FIGS. 1-3, access system 5 may be used to isolate, bypass and access the wall of a vascular structure. By way of example but not limitation, access system 5 may be used to isolate, bypass and access a lateral aneurysm 45 formed in the wall of a vascular structure 50. In this case, guidewire 35 is first deployed down vascular structure 50. Then access system 5, with proximal isolation barrier 10 and distal isolation barrier 15 set in their diametrically-reduced condition, is advanced over the guidewire to a point adjacent to lateral aneurysm 45. Next, proximal isolation barrier 10 and distal isolation barrier 15 are set in their diametrically-expanded condition, so as to conform to, and seal against, the wall of the vascular structure and thereby create an isolation zone 55 which encompasses lateral aneurysm 45. However, it will be appreciated that blood is still able to flow past the isolation zone (e.g., from flow zone 60 to flow zone 65) via bypass channel 20. To the extent that the proximal end of working catheter 30 is open to the atmosphere, blood in the isolation zone may flow out of the isolation zone via the working catheter and be replaced with air. Alternatively, the working catheter may be used to introduce another fluid (e.g., saline) into the isolation zone. At this point, instruments may be advanced through working catheter 30 so as to access, and provide therapy to, lateral aneurysm 45. Such instruments may include, but are not limited to, cutting instruments, biopsy instruments, closure instruments, material delivery systems, endoscopes, etc. At the conclusion of the procedure, proximal isolation barrier 10 and distal isolation barrier 15 are set in their diametrically-reduced condition, and then access system 5 is withdrawn along guidewire 35. Finally, guidewire 35 is removed from vascular structure 50.

Any debris created in isolation zone 55 during the procedure may be removed by withdrawing blood/debris from isolation zone 55. In one form of the invention, blood/debris evacuation may be effected by applying suction via working catheter 30 while both proximal isolation barrier 10 and distal isolation barrier 15 remain erected. In another form of the invention, blood/debris evacuation may be effected by first returning proximal isolation barrier 10 to its diametrically-reduced configuration while retaining distal isolation barrier 15 in its diametrically-expanded configuration, then removing blood/debris via suction, and then returning distal isolation barrier 15 to its diametrically-reduced configuration so that access system 5 may be removed from the vascular structure. This latter approach may be particularly applicable to angioplasty in the coronary and/or carotid arteries.

Figure 4:
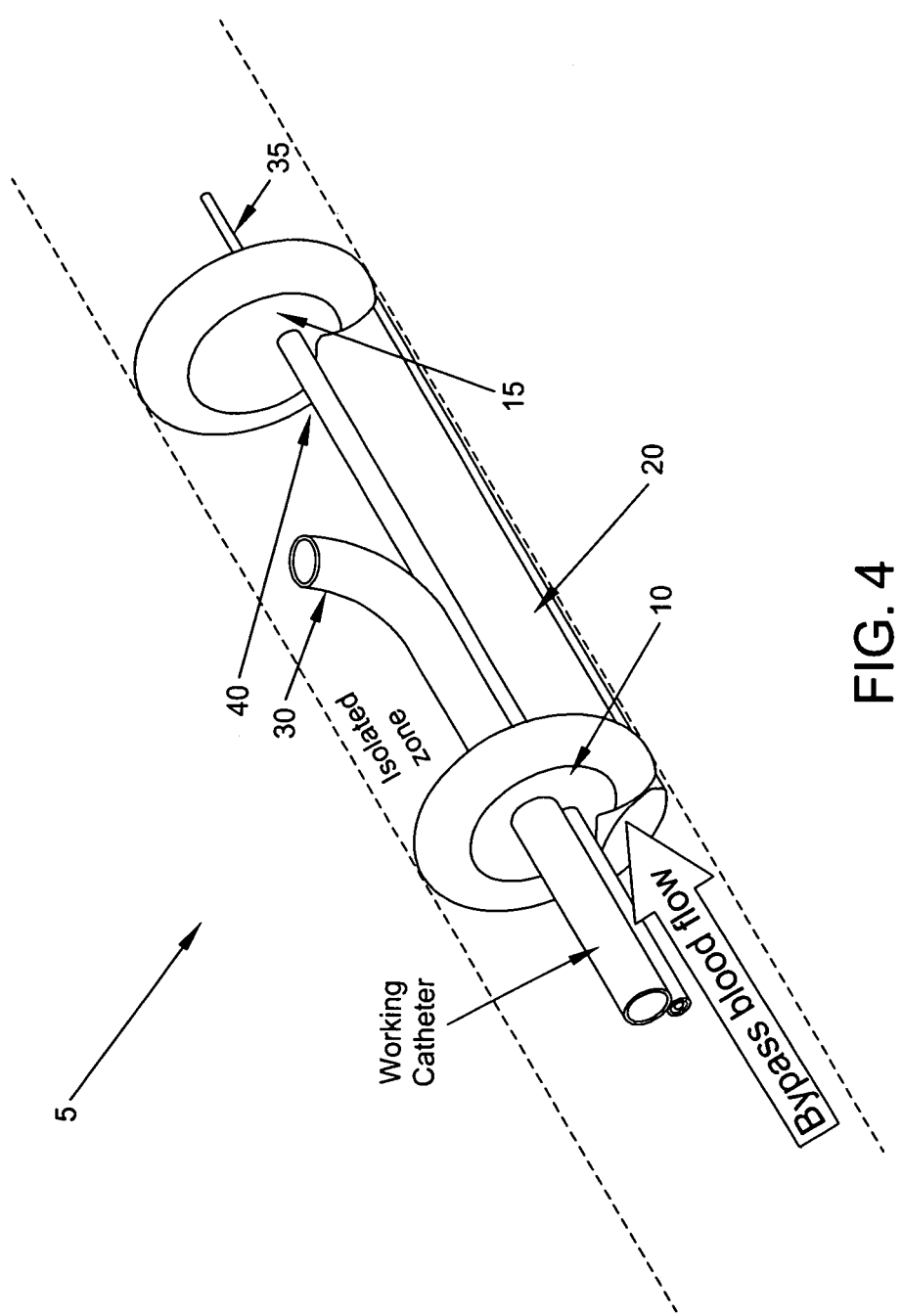
FIG. 4 is a schematic perspective view showing an alternative form of an access system deployed within a vascular structure.
Figure 5:
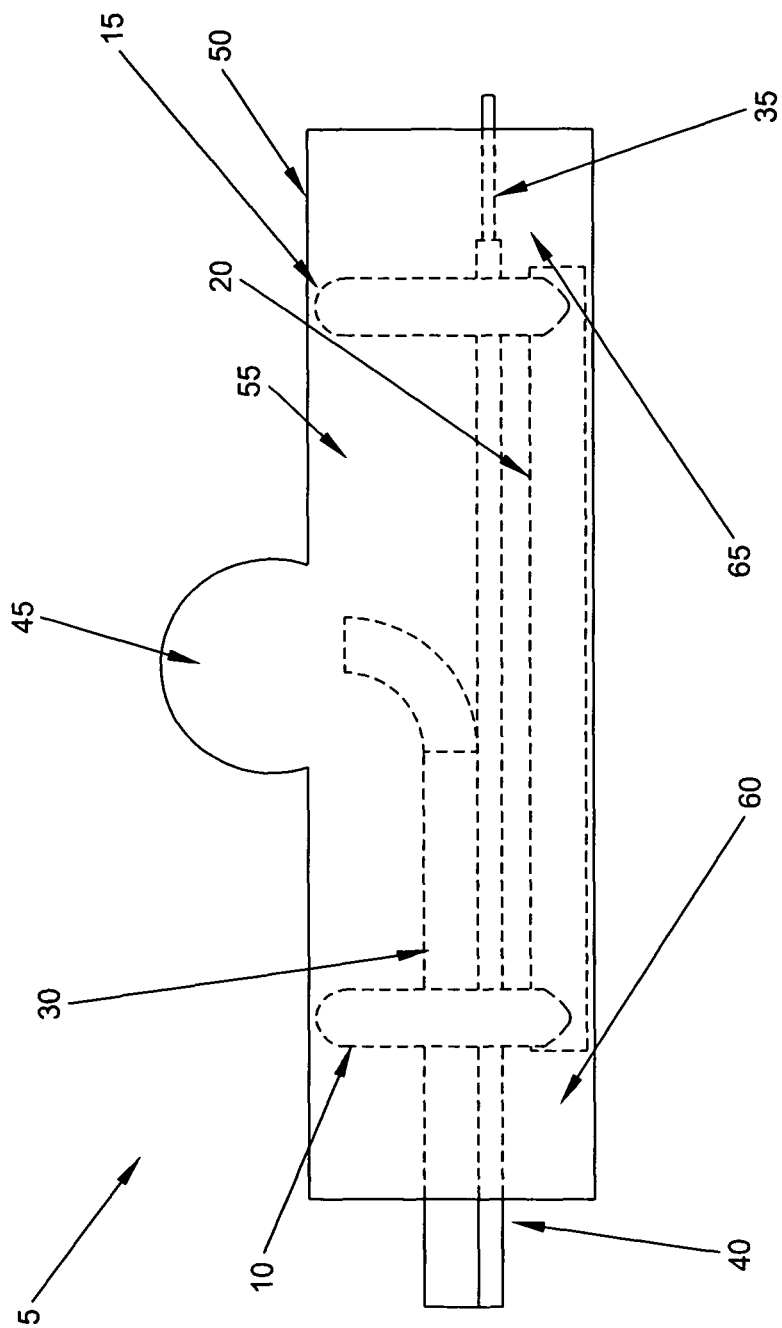
FIG. 5 is a schematic side view showing the access system of FIG. 4 deployed within a vascular structure, wherein the vascular structure includes an aneurysm.
Figure 13:
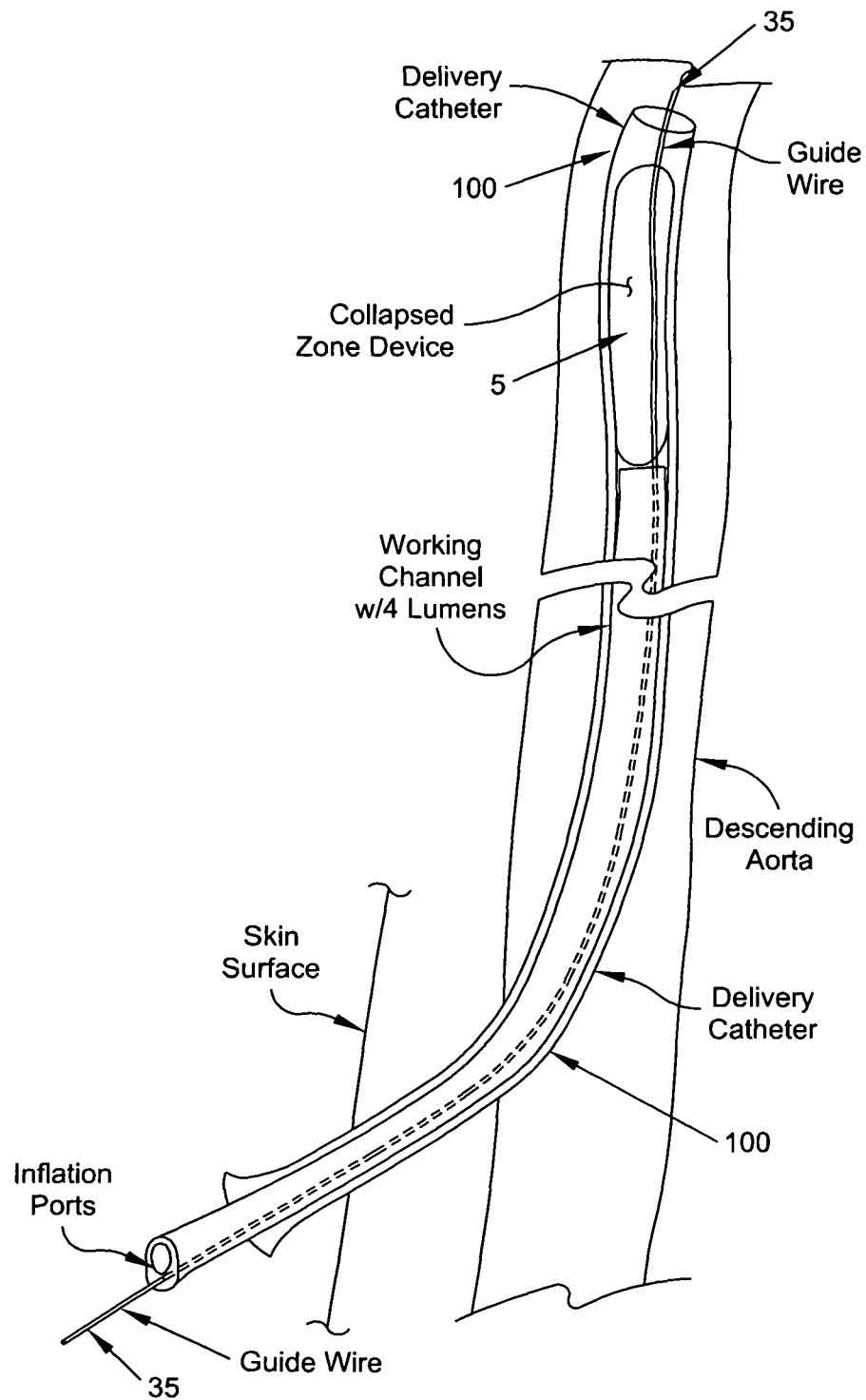

FIGS. 4 and 5 show an alternative form of access system 5. The access system shown in FIGS. 4 and 5 is substantially the same as the access system shown in FIGS. 1-3, except that guidewire channel 40 extends parallel to, but spaced from, bypass channel 20 and bypass channel 20 is positioned diametrically outboard so as to sit proximate to the wall of the vascular structure.

If desired, working catheter 30 may be made detachable from the remainder of access system 5. This feature can be advantageous where longer term isolation of a vascular region is desired, e.g., for aneurysm embolization, since it allows the relatively large-bore working catheter to be removed, leaving only the zone isolation apparatus and fluid bypass apparatus present in the body lumen.

As noted above, proximal isolation barrier 10 and distal isolation barrier 15 are designed so as to be able to assume a diametrically-expanded configuration or a diametrically-reduced configuration. As also noted above, proximal isolation barrier 10 and distal isolation barrier 15 may comprise an inflatable/deflatable balloon or a compressible/expandable ring, etc. In this respect it should be appreciated that where proximal isolation barrier 10 and distal isolation barrier 15 comprise an inflatable/deflatable balloon, the balloon may extend across substantially the entire diameter of the vascular structure. Alternatively, the balloon may extend only about the periphery of the diameter of the vascular structure, and a membrane 67 may extend across the interior of the balloon, such as is shown in FIG. 3. A similar construction may be used where proximal isolation barrier 10 and distal isolation barrier 15 comprise a compressible/expandable ring, e.g., such as one formed from a superelastic shape memory alloy. Again, a membrane may extend across the interior of the ring.

FIGS. 6-9 show an alternative form of access system 5. The access system shown in FIGS. 6-9 is substantially the same as the access system shown in FIGS. 1-3 except that proximal isolation barrier 10 and distal isolation barrier 15 comprise multi-segmented balloons 70, and working catheter 30 includes an opening 75 connected to the lumen of working catheter 30. The use of these multi-segmented balloons 70 to form proximal isolation barrier 10 and distal isolation barrier 15 provide a wider, more stable barrier without restricting blood flow through bypass channel 20. As seen in FIG. 9, channels 80 may be provided between adjacent balloons so that the interior of the balloons are in communication with one another.

FIGS. 10-12 show an alternative form of access system 5. The access system shown in FIGS. 10-12 is substantially the same as the access system shown in FIGS. 6-9 except that channels 80 may be replaced with holes 85 so that the interior of the balloons are in communication with one another.

Deployment

Figure 14:
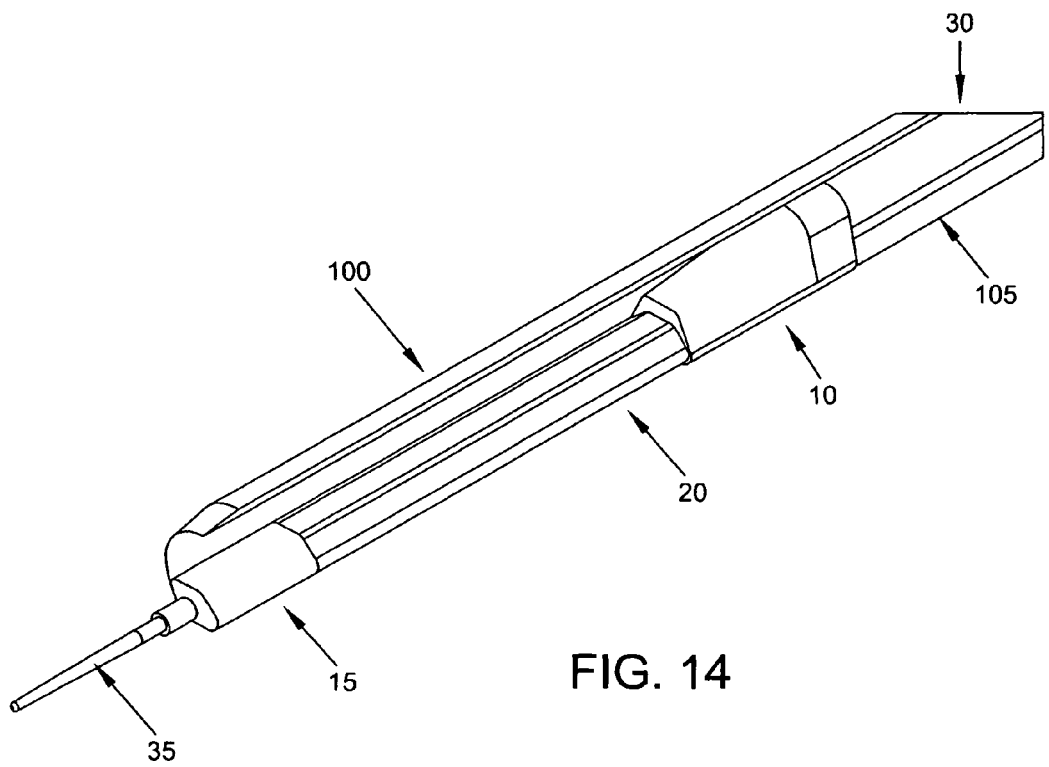
Figure 14A:
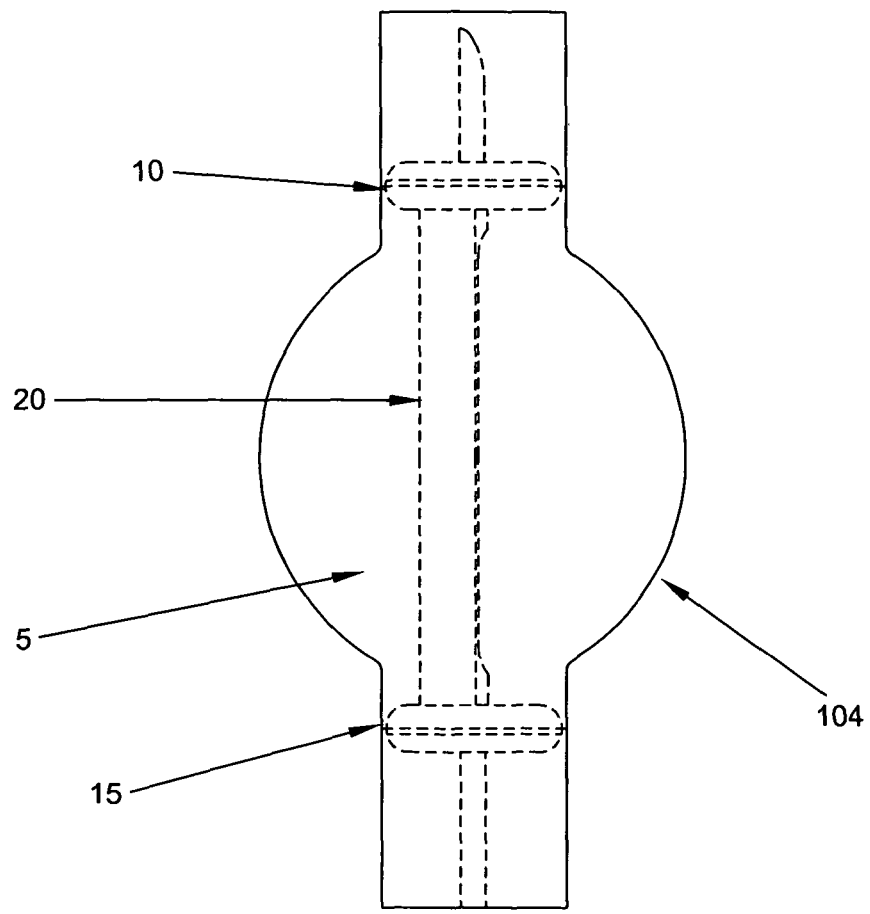
Figure 15:
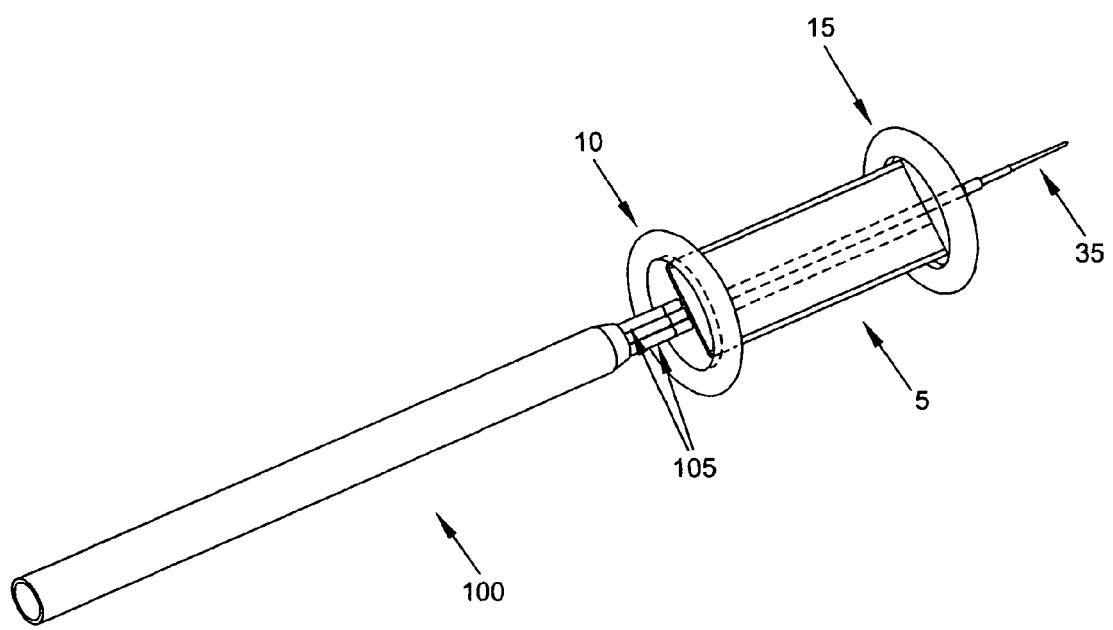
Figure 16:
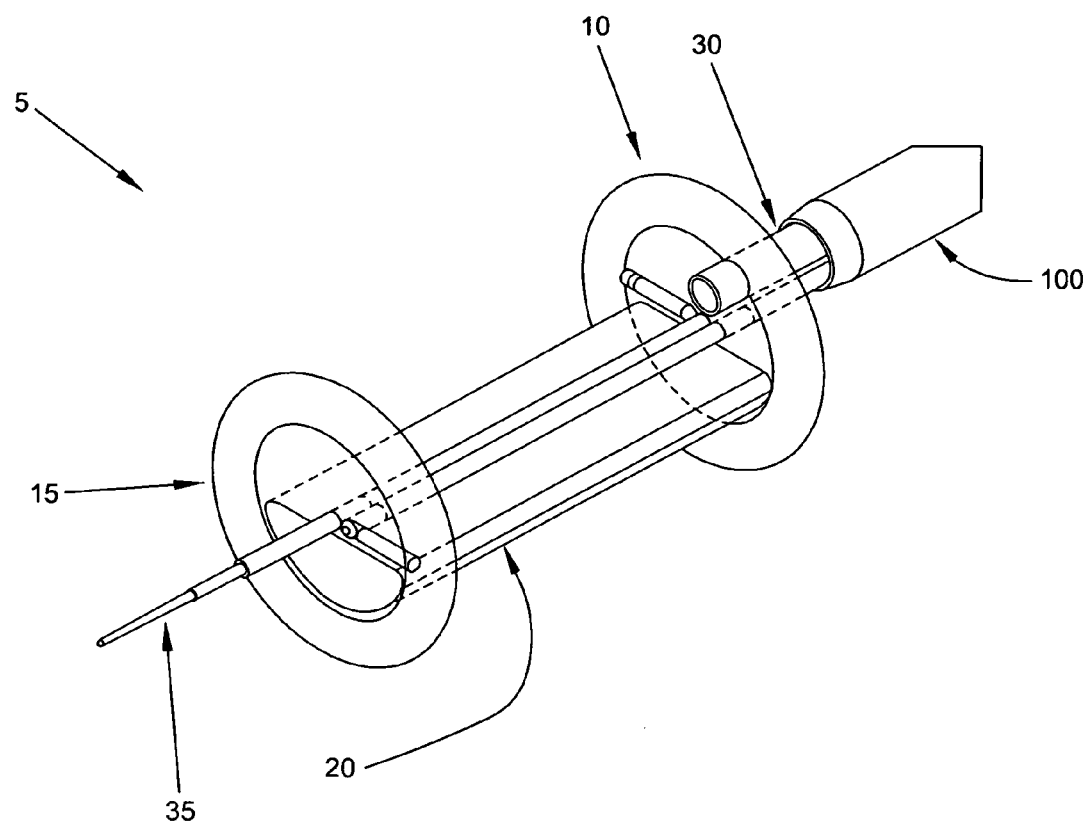

Access system 5 may be deployed in a vascular structure or other body lumen using a delivery catheter. More particularly, and looking next at FIGS. 13, 14, 14A and 15-20, a delivery catheter 100 comprising a delivery sheath 103 may be provided for advancing access system 5 to a procedure site within a vascular structure (or other body lumen), and for erecting access system 5 in the manner previously discussed. Furthermore, delivery catheter 100 may be used for advancing instruments down to the procedure site and/or removing debris from the procedure site (e.g., a fusiform aortic aneurysm 104 of the type shown in FIG. 14A), again in the manner previously discussed. Finally, delivery catheter 100 may be used to collapse access system 5 and remove it from the vascular structure (or other body lumen). In the case where access system 5 comprises inflatable/deflatable balloons in its proximal isolation barrier and/or distal isolation barrier 15, delivery catheter 100 may contain one or more fluid supply tubes 105 for inflating/deflating the balloons. It should be appreciated that delivery sheath 103 of delivery catheter 100 may also perform the function of an introducer sheath, in the sense that it can be secured to the exterior tissue of the patient once the delivery catheter is properly positioned. A hemostatic valve 110, with a side port 115, is preferably located on the proximal end of the delivery catheter to prevent the loss of blood through the catheter while still allowing the insertion of access system 5.

Anatomical Applications

It should be appreciated that access system 5 can be used to provide a wide range of therapies to vascular structures, e.g., aneurysm therapy, lesion therapy, infusion therapy, gene therapy, photodynamic therapy, etc. Access system 5 may also be used to repair tears, flaps and leaks in a vascular structure.

Furthermore, it should be also be appreciated that the present invention can be used to access structures other than vascular structures, e.g., the esophagus, stomach, small or large bowel, ureter, bladder, urethra, bronchus, bile duct, ear, nose, fallopian tube, other tubular or hollow structures within the human body, etc. In essence, the present invention can be advantageously used in substantially any body lumen where isolation, access and/or fluid bypass are desired. Additionally, it should be appreciated that the zone which is isolated between the proximal and distal isolation barriers could be of varying lengths, and of various diameters as well. Furthermore, many different catheter shapes and sizes may be utilized.

Without limiting the breadth and scope of the present invention, it is anticipated that the present invention is particularly well suited for treating fusiform aneurysms in the aorta and the larger peripheral blood vessels.

Furthermore, without limiting the breadth and scope of the present invention, it is anticipated that the present invention is particularly well suited for treating vascular trauma in a variety of situations where zone isolation and distal perfusion are both desirable and/or necessary, e.g., where vascular trauma needs to be temporarily stabilized while the patient is transported to another site for further treatment.

Modifications

While the present invention has been described in terms of certain exemplary preferred embodiments, it will be readily understood and appreciated by one of ordinary skill in the art that it is not so limited, and that many additions, deletions and modifications may be made to the preferred embodiments discussed above while remaining within the scope of the present invention.

What is claimed is:
1. Apparatus for accessing the wall of a body lumen while simultaneously providing zone isolation and fluid bypass capability, the apparatus comprising:
   an erectable proximal isolation barrier capable of making a sealing engagement with the wall of the body lumen;
   an erectable distal isolation barrier capable of making a sealing engagement with the wall of the body lumen;
   a bypass tube secured to, and extending between, the proximal isolation barrier and the distal isolation barrier, the bypass tube comprising a lumen communicating with an area of the body lumen proximal to the proximal isolation barrier and with an area of the body lumen distal to the distal isolation barrier so that fluid may pass from the area of the body lumen proximal to the proximal isolation barrier through the bypass tube to the area of the body lumen distal to the distal isolation barrier;
   a working tube being spaced from, and being formed separately from, the bypass tube and passing through the proximal isolation barrier, through the distal isolation barrier, and terminating in the area of the body lumen distal to the distal isolation barrier, the working tube comprising a lumen communicating with an area proximal to the proximal isolation barrier and with the area between the proximal isolation barrier and the distal isolation area, the working tube comprising a slot communicating with the lumen of the working tube, the slot having a length greater than its width and being sized and configured to provide an opening for instruments to pass through in order to access a portion of the wall of the body lumen positioned between the proximal isolation barrier and the distal isolation barrier; and a guidewire tube being formed separately from the bypass tube and the working tube, the guidewire tube being positioned in the lumen of the working tube so that the guidewire tube extends through the proximal isolation barrier, through the distal isolation barrier, and terminates in the area of the body lumen distal to the distal isolation barrier;

wherein the diameter of the bypass tube is greater than the diameter of the working tube and the diameter of the working tube is greater than the diameter of the guidewire tube.

2. Apparatus according to claim 1 wherein the body lumen comprises a vascular structure.

3. Apparatus according to claim 1 wherein the body lumen comprises one selected from the group consisting of the esophagus, stomach, small or large bowel, ureter, bladder, urethra, bronchus, bile duct, ear, nose and fallopian tube.

4. Apparatus according to claim 1 wherein the erectable proximal isolation barrier and the erectable distal isolation barrier are constructed so as to be capable of assuming a diametrically-reduced configuration and a diametrically-expanded configuration, and further wherein the erectable proximal isolation barrier and the erectable distal isolation barrier are in their diametrically-expanded configuration when making a sealing engagement with the wall of the body lumen.

5. Apparatus according to claim 1 wherein at least one of the erectable proximal isolation barrier and the erectable distal isolation barrier comprises an upstream isolation barrier, and further wherein the upstream isolation barrier is configured to channel blood flow into the bypass tube.

6. Apparatus according to claim 1 wherein the proximal isolation barrier comprises an inflatable/deflatable balloon.

7. Apparatus according to claim 6 wherein the inflatable/deflatable balloon comprises a torus with a membrane closing off its center opening.

8. Apparatus according to claim 6 wherein the proximal isolation barrier comprises a plurality of inflatable/deflatable balloons.

9. Apparatus according to claim 8 wherein the balloons communicate with one another.

10. Apparatus according to claim 1 wherein the proximal isolation barrier comprises a compressible/expandable superelastic shape memory alloy ring.

11. Apparatus according to claim 10 wherein the compressible/expandable superelastic shape memory alloy ring comprises a torus with a membrane closing off its center opening.

12. Apparatus according to claim 1 wherein the distal isolation barrier comprises an inflatable/deflatable balloon.

13. Apparatus according to claim 12 wherein the inflatable/deflatable balloon comprises a torus with a membrane closing off its center opening.

14. Apparatus according to claim 12 wherein the distal isolation barrier comprises a plurality of inflatable/deflatable balloons.

15. Apparatus according to claim 14 wherein the balloons communicate with one another.

16. Apparatus according to claim 1 wherein the distal isolation barrier comprises a compressible/expandable superelastic shape memory alloy ring.

17. Apparatus according to claim 16 wherein the compressible/expandable superelastic shape memory alloy ring comprises a torus with a membrane closing off its center opening.

18. Apparatus according to claim 1 wherein the working tube is releasably secured to the proximal isolation barrier.

19. A method for accessing the wall of a body lumen while simultaneously providing zone isolation and fluid bypass capability, the method comprising:

providing an access system comprising:
an erectable proximal isolation barrier capable of making a sealing engagement with the wall of the body lumen;
an erectable distal isolation barrier capable of making a sealing engagement with the wall of the body lumen;
a bypass tube secured to, and extending between, the proximal isolation barrier and the distal isolation barrier, the bypass tube comprising a lumen communicating with an area of the body lumen proximal to the proximal isolation barrier and with an area of the body lumen distal to the distal isolation barrier so that fluid may pass from the area of the body lumen proximal to the proximal isolation barrier through the bypass tube to the area of the body lumen distal to the distal isolation barrier;
a working tube being spaced from, and being formed separately from, the bypass tube and passing through the proximal isolation barrier, through the distal isolation barrier, and terminating in the area of the body lumen distal to the distal isolation barrier, the working tube comprising a lumen communicating with an area proximal to the proximal isolation barrier and with the area between the proximal isolation barrier and the distal isolation area, the working tube comprising a slot communicating with the lumen of the working tube, the slot having a length greater than its width and being sized and configured to provide an opening for instruments to pass through in order to access a portion of the wall of the body lumen positioned between the proximal isolation barrier and the distal isolation barrier; and
a guidewire tube being formed separately from the bypass tube and the working tube, the guidewire tube being positioned in the lumen of the working tube so that the guidewire tube extends through the proximal isolation barrier, through the distal isolation barrier, and terminates in the area of the body lumen distal to the distal isolation barrier;
wherein the diameter of the bypass tube is greater than the diameter of the working tube and the diameter of the working tube is greater than the diameter of the guidewire tube;
deploying the access system within the body lumen;
erecting the distal isolation barrier and the proximal isolation barrier so that the distal isolation barrier and the proximal isolation barrier make sealing engagements with the wall of the body lumen; and
inserting an instrument into the working tube and through the slot in the working tube so as to access the wall of the body lumen through the working tube.

20. A method according to claim 19 wherein the body lumen comprises a vascular structure.

21. A method according to claim 19 wherein the body lumen comprises one selected from the group consisting of the small bowel, ureter, urethra, bronchus, bile duct, ear, nose and fallopian tube.

22. A method according to claim 19 wherein the erectable proximal isolation barrier and the erectable distal isolation barrier are constructed so as to be capable of assuming a diametrically-reduced configuration and a diametrically-expanded configuration, and further wherein the erectable proximal isolation barrier and the erectable distal isolation barrier are in their diametrically-expanded configuration when making a sealing engagement with the wall of the body lumen.

23. A method according to claim 19 wherein at least one of the erectable proximal isolation barrier and the erectable distal isolation barrier comprises an upstream isolation barrier, and further wherein the upstream isolation barrier is configured to channel blood flow into the bypass tube.

24. A method according to claim 19 further comprising performing therapy on the wall of the body lumen.

25. A method according to claim 24 wherein the therapy comprises treating a lesion on the wall of the body lumen.

26. A method according to claim 24 wherein the therapy comprises treating an aneurysm on the wall of the body lumen.

27. A method according to claim 26 wherein the aneurysm comprises at least one from the group consisting of a fusiform aneurysm and a lateral aneurysm.

28. A method according to claim 26 wherein the aneurysm is located in one from the group consisting of the aorta, an iliac branch and a femoral artery.

29. A method according to claim 24 wherein the therapy comprises taking a biopsy.

30. A method according to claim 24 wherein the therapy comprises infusion therapy.

31. A method according to claim 24 wherein the therapy comprises gene therapy.

32. A method according to claim 24 wherein the therapy comprises repairing at least one of a tear, a flap and a leak in the body lumen.

33. A method according to claim 24 wherein the therapy comprises the insertion, placement and visualization of material that repairs the body lumen.

34. A method according to claim 19 wherein the proximal isolation barrier comprises an inflatable/deflatable balloon.

35. A method according to claim 34 wherein the inflatable/deflatable balloon comprises a torus with a membrane closing off its center opening.

36. A method according to claim 34 wherein the proximal isolation barrier comprises a plurality of inflatable/deflatable balloons.

37. A method according to claim 36 wherein the balloons communicate with one another.

38. A method according to claim 19 wherein the proximal isolation barrier comprises a compressible/expandable superelastic shape memory alloy ring.

39. A method according to claim 38 wherein the compressible/expandable superelastic shape memory alloy ring comprises a torus with a membrane closing off its center opening.

40. A method according to claim 19 wherein the distal isolation barrier comprises an inflatable/deflatable balloon.

41. A method according to claim 40 wherein the inflatable/deflatable balloon comprises a torus with a membrane closing off its center opening.

42. A method according to claim 40 wherein the distal isolation barrier comprises a plurality of inflatable/deflatable balloons.

43. A method according to claim 42 wherein the balloons communicate with one another.

44. A method according to claim 19 wherein the distal isolation barrier comprises a compressible/expandable superelastic shape memory alloy ring.

45. A method according to claim 44 wherein the compressible/expandable superelastic shape memory alloy ring comprises a torus with a membrane closing off its center opening.

46. A method according to claim 19 wherein the access system is deployed into the body lumen over a guidewire.

47. A method according to claim 19 comprising the additional step of detaching the working tube from the proximal isolation barrier.

48. A method according to claim 19 further comprising removing debris from the body lumen.

49. A method according to 48 wherein the debris is removed while the proximal isolation barrier and the distal isolation barrier are erected.

50. A method according to 49 wherein the debris is removed by applying suction through the working tube.

51. A method according to claim 48 wherein the erectable proximal isolation barrier is constructed so as to be capable of assuming a diametrically-reduced configuration and a diametrically-expanded configuration, wherein the erectable proximal isolation barrier is placed in its diametrically-expanded configuration when making a sealing engagement with the wall of the body lumen, and further wherein the erectable proximal isolation barrier is placed in its diametrically-reduced configuration before the debris is removed.

52. A method according to claim 19 wherein the native fluid located between the erectable distal isolation barrier and the erectable proximal isolation barrier is replaced with a substitute fluid.

53. A method according to claim 52 wherein the substitute fluid comprises saline.

54. A method according to claim 52 wherein the substitute fluid comprises air.

55. A method according to claim 52 wherein an endoscope is advanced to the zone located between the proximal isolation barrier and the distal isolation barrier via the working tube.

* * * * *